United States Patent [19]

McIntyre

[11] 3,969,629

[45] July 13, 1976

[54] X-RAY TREATMENT MACHINE HAVING MEANS FOR REDUCING SECONDARY ELECTRON SKIN DOSE

[75] Inventor: Raymond D. McIntyre, Los Altos Hills, Calif.

[73] Assignee: Varian Associates, Palo Alto, Calif.

[22] Filed: Mar. 14, 1975

[21] Appl. No.: 558,392

[52] U.S. Cl. ............................... 250/503; 250/508
[51] Int. Cl.² .......................................... G01J 1/00
[58] Field of Search .......... 250/505, 508, 509, 396, 250/398, 503

[56] References Cited
UNITED STATES PATENTS

| 3,482,136 | 12/1969 | Herrera | 250/396 |
| 3,614,424 | 10/1971 | Openshaw | 250/505 |

*Primary Examiner*—Alfred E. Smith
*Assistant Examiner*—B. C. Anderson
*Attorney, Agent, or Firm*—Stanley Z. Cole; Leon F. Herbert

[57] ABSTRACT

In an x-ray treatment machine a charged particle accelerator or cobalt source is provided for producing a field of high energy x-ray radiation for application to a body, for treatment thereof. The radiation machine includes collimators and field shaping structures for shaping the field of x-ray radiation applied to the body. The high energy x-ray radiation intercepted by the field shaping and collimating structures produces high energy secondary electrons by a number of different atomic processes. These energetic secondaries contaminate the shaped radiation field applied to the body being treated. The contaminating high energy electrons, if not eliminated, substantially increase the dosage of radiation delivered to the surface of the body. However, electron deflecting means, such as magnet structures, are provided for interposing in the electron contaminated field of x-ray radiation, so as to provide an electron deflecting flux for deflecting the contaminating electrons and reducing the dose due to these electrons by spreading them out more uniformly over the treated surface. In addition, an electron absorbing screen is interposed in the secondary electron contaminated radiation field for further absorbing the unwanted high energy secondary electrons.

9 Claims, 6 Drawing Figures

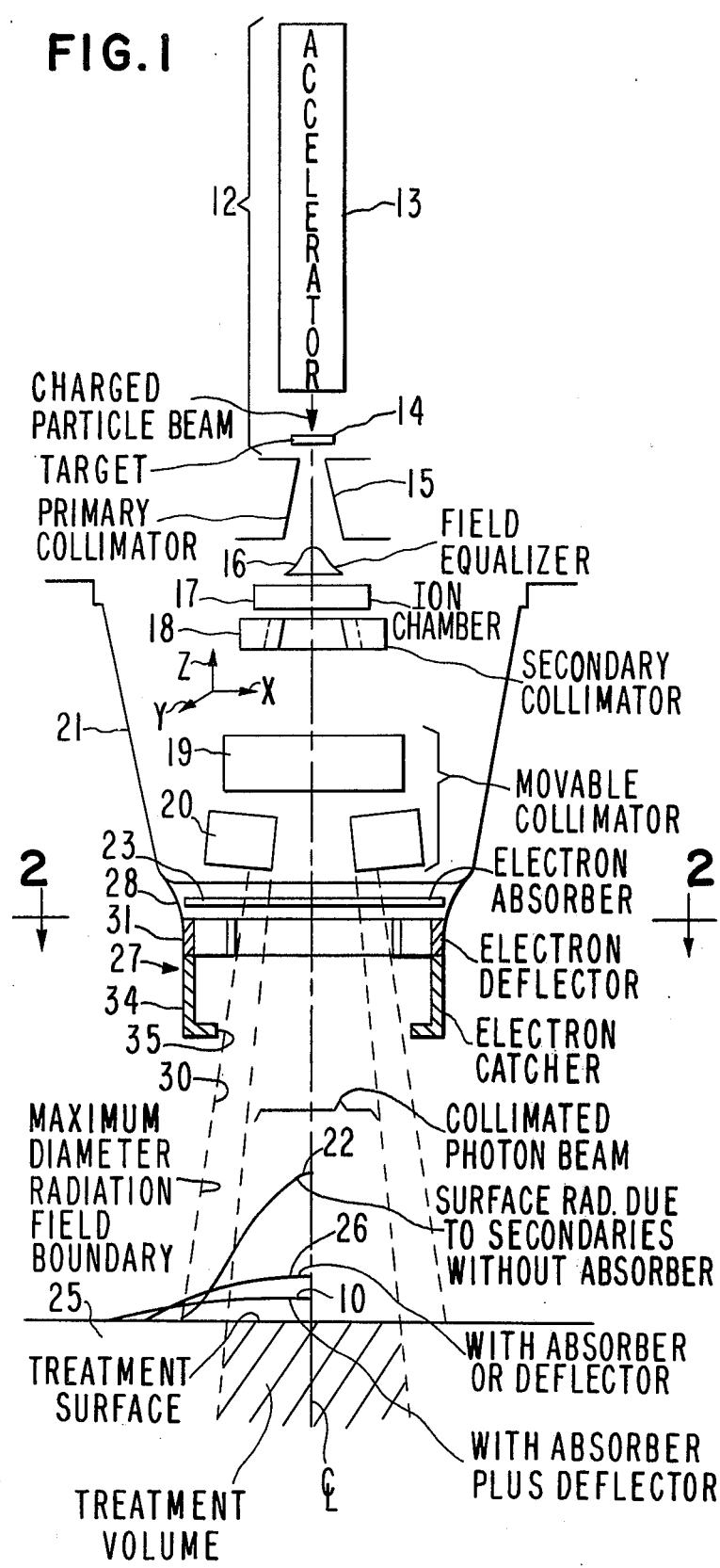

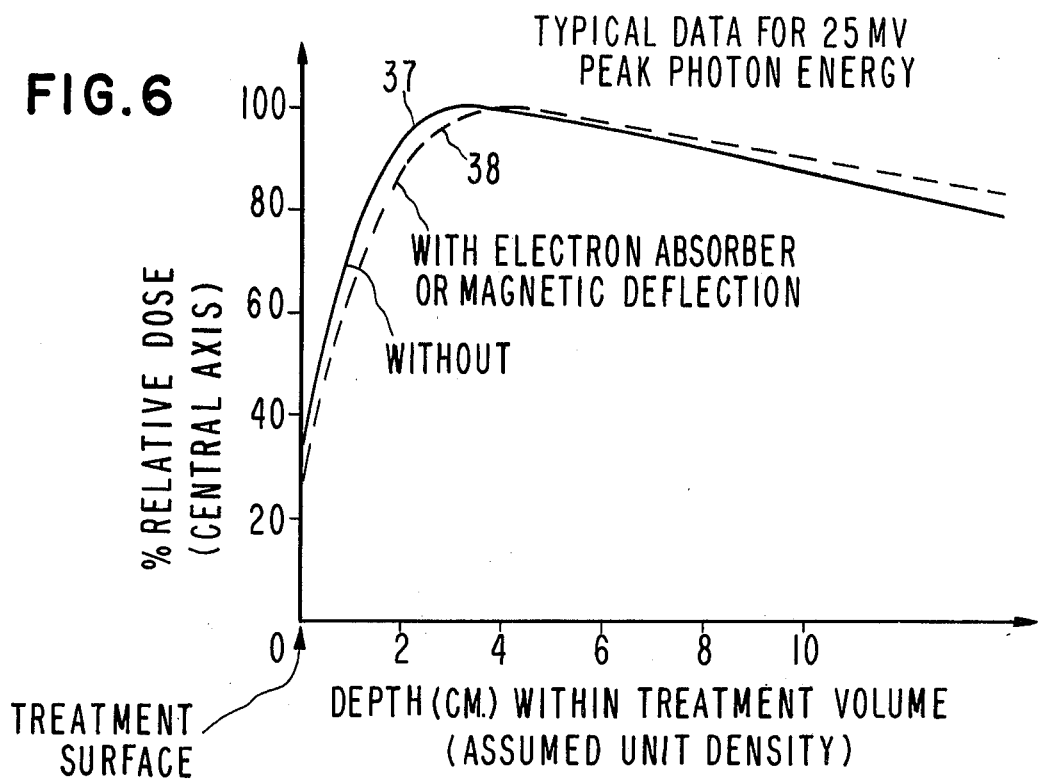
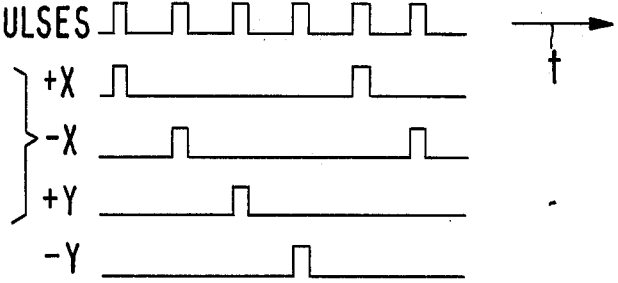
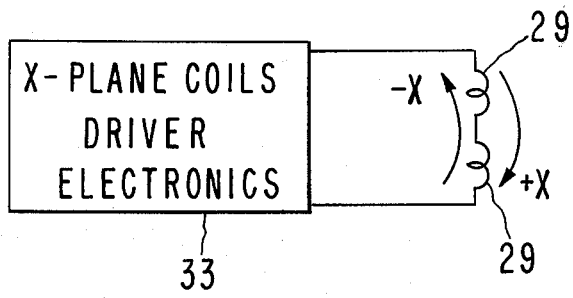

3,969,629

X-RAY TREATMENT MACHINE HAVING MEANS FOR REDUCING SECONDARY ELECTRON SKIN DOSE

BACKGROUND OF THE INVENTION

The present invention relates in general to x-ray treatment machines and, more particularly, to such machines having means for reducing the secondary electron contamination of the radiation field applied to the body being treated, thereby reducing the surface radiation dose rate.

DESCRIPTION OF THE PRIOR ART

Heretofore, it has been proposed in x-ray therapy machines to provide an electron absorber screen, as of tin, in the secondary electron contaminated field of radiation applied to the patient for absorbing the high energy contaminating secondary electrons to reduce the radiation dose rate being delivered to the skin of the patient being treated. Such a prior art system is disclosed in an article entitled "Effect of Various Atomic Number Absorbers on Skin Dose for 10-MeV X-Rays" appearing in *Radiology*, Volume 109, pp. 209–212 of October 1973.

While a secondary electron absorber serves to reduce the radiation dose rate delivered to the surface of the body being treated, it also attenuates the x-ray radiation field applied to the body being treated. Thus, it is desirable to provide an improved means for reducing the maximum radiation dose rate delivered to the surface of the body being treated due to high energy secondary electron contamination of the radiation field.

SUMMARY OF THE PRESENT INVENTION

The principal object of the present invention is the provision of an improved x-ray treatment machine having means for reducing secondary electron surface radiation dose rate.

In one feature of the present invention, an electron deflecting flux is interposed in the electron contaminated field of the x-ray radiation field to be applied to the body being treated, for deflecting the contaminating electron trajectories and spreading their radiation dose out more uniformly over the treated surface, whereby the maximum surface radiation dose rate, due to contaminating secondary electrons, is reduced in use.

In another feature of the present invention, the means for producing the electron deflecting flux comprises a magnet structure for producing an electron deflecting magnetic flux in the electron contaminated field for deflecting and spreading out the contaminating secondary electron trajectories.

In another feature of the present invention, a catching and absorbing structure is disposed downstream of the interposed secondary electron deflecting flux for intercepting and absorbing some proportion of the deflected contaminating secondary electrons.

In another feature of the present invention, a high energy secondary electron absorber screen is used in conjunction with an electron deflecting means for still further reduction of the contaminating high energy secondary electrons in the radiation field.

Other features and advantages of the present invention will become apparent upon a perusal of the following specification taken in connection with the accompanying drawings wherein:

BRIEF DESCRIPTION OF THE DRAWINGS

FIG. 1 is a longitudinal sectional view, partly schematic, of a radiation therapy machine incorporating features of the present invention, FIG. 2 is a sectional view of a portion of the structure of FIG. 1 taken along line 2—2 in the direction of the arrows, FIG. 3 is a detail view of an alternative embodiment of a portion of the structure of FIG. 1 delineated by line 3—3, FIG. 4 is a timing diagram depicting the waveforms applied to the accelerator and to the magnetic electron deflecting coil structure of FIG. 1, FIG. 5 is a schematic circuit diagram for the magnetic coil driver portion of the magnetic electron deflecting structure of FIG. 1, and FIG. 6 is a plot of relative radiation dose on the central axis of the radiation field versus depth within the treatment volume depicting the reduction in surface radiation dose rate obtained with the electron absorber or electron deflection system of the present invention.

DESCRIPTION OF THE PREFERRED EMBODIMENTS

Referring now to FIG. 1, there is shown a radiation therapy machine 11 incorporating features of the present invention. The radiation therapy machine 11 includes a source of x-ray radiation 12. In a typical example, the x-ray radiation field to be applied to the patient or body being treated has a mean photon energy in the range 2 to 6MV. The radiation source 12 may comprise a cobalt source or a particle accelerator 13. In the latter case, a charged particle electron accelerator accelerates a beam of electrons to a relatively high mean energy as of between 4 to 25 MeV and directs this beam of particles into an x-ray converter or target 14, to produce a lobe of x-ray radiation extending out from the target 14 generally in the direction representing an extension of the incident beam of charged particles.

A primary radiation field collimator 15, as of lead or tungsten, is disposed adjacent the target 14 for providing primary collimation to the field of x-ray radiation. A field equalizer 16 is disposed downstream of the primary colllimator 15 for obtaining a more uniform distribution of the x-ray radiation within the collimated field. An ion chamber 17 is disposed downbeam of the field equalizer 16, for measuring the intensity of the radiation field. A secondary field collimator 18 is disposed downbeam of the ion chamber for further collimation of the beam of x-ray radiation. Finally, a pair of movable collimator jaws 19 and 20 as of lead or tungsten, are provided for adjusting the boundaries of the field of radiation passable therethrough. The movable collimators 19 and 20 generally include two sets of jaws. The first set of jaws 19 is movable in the Y-direction for determining the extent of the field of radiation in the Y-direction, whereas the second set of movable jaws 20 is movable in the X-direction for determining the maximum extent of the field boundary in the X-direction. A housing 21 encloses the primary collimator, field equalizer, ion chambers, and secondary and final collimators.

As the x-ray radiation passes through the various field shapers and collimators, it is intercepted by the field shaping and collimating structures resulting in the production of high energy secondary electrons due to interaction between the x-ray photons and the atomic structure of the collimator materials. Thus the resultant field of x-ray radiation emergent from the collimator assembly is contaminated with high energy secondary electrons. These high energy secondary electrons which, in the case of a mean radiation photon energy of 6MV, will typically have energies of up to approximately 3 MeV. These energetic secondary electrons, when directed onto the surface of the body to be treated, will be absorbed within a thin layer of body surface tissue, resulting in burning of the skin of a patient being treated for deep-seated tumors by the radiation field. For example, curve 22 shows the surface radiation dose rate due to contaminating electrons, as a function of distance from the centerline of the radiation field. As can be seen by curve 22, the surface radiation dose rate, the distribution of contaminating electrons peaks up in the center of the radiation field and falls off toward the outer periphery thereof.

To reduce the surface radiation dose rate, due to contaminating electrons, an electron absorber plate 23, which may be of aluminum or preferably of tin, is disposed downbeam of the collimator structures in the secondary electron contaminated radiation field for absorbing the unwanted secondary electrons while providing a relatively high transmittance therethrough of the desired x-ray radiation directed onto the body 25 for treatment thereof. In a typical example of an aluminum electron absorber plate 23, the plate thickness is approximately 0.25 inch. With the provision of the absorber plate 23, the surface radiation dose rate at the centerline of the radiation field at the surface due to contaminating electrons is substantially reduced to that shown by curve 26. Curve 26 has a value on the centerline which is approximately 20% of the value of curve 22. Thus, the absorber 23 results in a significant reduction in the surface radiation dose rate, especially in the center of the radiation field. Optimum absorber results are obtained for an absorber material having an atomic number near 50, such as tin.

The surface radiation dose rate due to the contaminating high energy secondary electrons is reduced further by providing an electron deflector structure 27 downbeam of the electron absorber 23. The electron absorber 23 and the electron deflector 27 are coupled to and carried from the housing via a bracket 28. The electron deflector 27 includes a four pole electronmagnetic arrangement for producing a sequence of electron deflection magnetic flux pulses interposed in the electron contaminated field of radiation. The magnetic flux first extends in the X-direction and then in the Y-direction and is alternated in polarity so that the electrons are spread out more uniformly over the entire radiation field at the surface of the body being treated. The four pole structure 27 is shown in greater detail in FIG. 2 and includes four electromagnets 29 coupled at their outer end by a common ferromagnetic yoke 31, as of soft iron. Each electromagnet 29 includes an internal pole piece 32 disposed just outside of the maximum radiation field boundary, as determined by the collimators 19 and 20.

Referring now to FIGS. 4 and 5, there is shown the sequence for polarization of the electromagnets 29 as a function of the accelerator trigger pulses applied to the accelerator 13 for generating the pulses of x-ray radiation. More particularly, the pulse of current for driving one of the pairs of electromagnets 29, such as the x-pair, as derived from an x-plane coil driver circuit 33 is synchronized with a trigger pulse supplied to the accelerator 13 for generating a pulse of high energy charged particles resulting in a pulse of x-ray radiation. The pulsed coil driver current first flows through coils 29 in a direction for generating a magnetic field extending between the pair of electromagnets 29 in plus X-direction. In the next pulse, the x-plane coil driver 33 reverses the current to the coils 29 so as to cause the magnetic field to extend in the minus X-direction. Thus, the contaminating secondary electrons are deflected back and forth relative to the centerline of the radiation field. In the next pulse, the y-coil driver, similar to the x-coil driver 33, but not shown, drives the y-set of electromagnets 29' first to produce a magnetic field in the plus Y-direction and in the next current pulse in the minus Y-direction. The sequence then repeats so that the unwanted secondary electrons are deflected away from the center of the field of radiation to produce a spreading out and thus a reduction in the maximum radiation dose rate on central axis as shown by curve 26. Curve 10 shows the additional reduction in the maximum dose rate obtained by the combination including the absorber plate 23 and the electron deflector 27.

A tubular electron catcher and absorber member 34, as of aluminum, depends from the four pole magnet structure 31 and includes an inwardly directed lower lip portion 35. The lip portion 35 of the tubular electron catcher and absorber 34 preferably conforms to the shape of the radiation field boundary 30 and is slightly spaced outwardly from the maximum radiation field boundary, as shown in FIG. 2. The electron catcher and absorber serves to catch and absorb the outwardly deflected electrons found near the perimeter of the maximum x-ray radiation field boundary.

Referring now to FIG. 6, there is shown a plot of relative radiation dose on the central axis of the radiation field as a function of the depth within the treated volume of the body 25. The solid curve 37 shows the relative radiation dose without the electron absorber 23 or the electron deflector 27, whereas the dashed curve 38 shows the radiation dose with the electron absorber 23 or the electron deflector 27. By comparison of the curves 37 and 38, it is seen that the radiation dose is substantially reduced at the treatment surface while actually increasing the radiation dose within the treatment volume, in the region beyond the depth of peak intensity.

Referring now to FIG. 3, there is shown an alternative embodiment of the electron deflector 27. More particularly, in FIG. 3 the electron deflector 27 comprises a pair of axially spaced sets of four pole magnets energized with permanent magnets 41. The yoke 31 extends around both axially spaced sets of magnets 41. The magnets in each set of four pole magnets are axially aligned with the other set. However, the polarities of the permanent magnets 41 are reversed in one set relative to those in the other set. As in the magnetic deflector 27 of FIG. 1, and electron catcher and absorber 34 depends from the yoke 31. The double four pole magnetic circuit serves to disperse or spread the electrons radially outward from the centerline of the radiation field 30.

As an alternative to a magnetic electron deflector 27, an electrostatic electron deflector 27 is employed. However, the magnetic deflector comprises the preferred embodiment. In a typical example of a magnetic deflector of a geometry as shown in FIG. 2, for deflecting high energy secondary electrons of an energy of approximately 3 MeV by approximately 6 cm, assuming a spacing of approximately 40 cm from the magnetic deflector 27 to the treatment surface, the magnets are energized to produce a magnetic field of approximately 350 gauss on the centerline of the radiation field.

What is claimed is:

1. In an x-ray treatment machine:
    means for producing a field of x-ray radiation for application to a body for treatment thereof;
    means for shaping the field of x-ray radiation as applied to the body, said field shaping means producing contamination of the radiation field of x-ray radiation with high energy secondary electrons which can substantially increase the undesirable electron portion of the total dosage of radiation delivered to the surface of the body being treated; and
    electron deflection means for interposing in the electron contaminated field of x-ray radiation an electron deflecting flux for deflecting the contaminating electron trajectories and spreading the electron radiation dose rate out more uniformly over the treated surface, whereby the maximum central axis surface radiation dose rate due to the irradiation of the body with contaminating secondary electrons is reduced in use.

2. The apparatus of claim 1 including, catching and absorbing means disposed downbeam of said interposed electron deflection flux and out of the shaped field of x-ray radiation for catching and absorbing the energy of the deflected contaminating electrons.

3. The apparatus of claim 1 including, absorber means interposed in the secondary electron contaminated field of x-ray radiation for absorbing said contaminating secondary electrons, whereby the surface radiation dose rate is further reduced in use.

4. The apparatus of claim 3 wherein said absorber means is made of a material selected from the group consisting of aluminum and tin.

5. The apparatus of claim 2 wherein said catching and absorbing means is made of aluminum.

6. The machine of claim 1 wherein said electron deflection means includes four electron deflecting flux-forming means substantially equally spaced around the axis of said field of X-radiation and arranged to provide flux forming polarity of opposite sense on opposite sides of the axis of said field of x-ray radiation.

7. The machine of claim 1 wherein said electron deflection means comprises a first set of electromagnets positioned on opposite sides of the axis of said field of X-radiation, a second set of electromagnets positioned on opposite sides of said axis and substantially orthogonal to said first set, and electrical means for periodically reversing the polarity of said first set and for periodically reversing the polarity of said second set.

8. The machine of claim 7 wherein said electrical means is arranged to energize said first and second sets of electromagnets sequentially.

9. The machine of claim 1 wherein said electron deflection means comprises a first set of four magnets substantially equally spaced around the axis of said field of x-ray radiation and having poles of opposite polarity on opposite sides of said axis, a second set of four magnets adjacent said first set along said axis and in substantial alignment with respective ones of said first set of magnets, and said substantially aligned magnets having their polarities reversed from the polarities of the respective magnets with which they are substantially aligned.

* * * * *